United States Patent [19]
Bouvet

[11] Patent Number: 5,037,441
[45] Date of Patent: Aug. 6, 1991

[54] ROTULE POUR PROTHESE

[75] Inventor: Jean-Claude Bouvet, La Ferte Alais, France

[73] Assignee: La Biomecanique Integree, France

[21] Appl. No.: 482,609

[22] Filed: Feb. 21, 1990

[30] Foreign Application Priority Data

Jun. 28, 1989 [FR] France ............................. 89 08598

[51] Int. Cl.⁵ .............................................. A61F 2/36
[52] U.S. Cl. ................................................... 623/23
[58] Field of Search ....................... 623/16, 18, 21, 22, 623/23

[56] References Cited

FOREIGN PATENT DOCUMENTS 0202141 11/1986 France .................................. 623/22
0660681 6/1987 Switzerland ......................... 623/23

Primary Examiner—David J. Isabella
Attorney, Agent, or Firm—Sughrue, Mion, Zinn, Macpeak & Seas

[57] ABSTRACT

The joint of the present invention is characterized essentially by the fact that it includes a male portion and a female portion, the male portion comprising a ball 13 and means 9, 10, 11, . . . for fixing the ball on a connection peg 4, and the female portion comprising a cup 17 having a concave spherical shape complementary to the shape of the ball, with the ball being made of a material having a crystalline structure, e.g. a monocrystal such as ruby, sapphire, or diamond. The invention is particularly suitable for hip prosthesis or the like.

13 Claims, 2 Drawing Sheets

ROTULE POUR PROTHESE

The present invention relates to a ball-and-socket for a prosthesis such as is implanted in the human body when a joint is damaged, for example due to illness or accident, and in particular the joint of the hip, the knee, etc.

Surgeons very often have to perform operations which consist in implanting prostheses, and the commonest implants concern the hip or the knee. Due to accident or illness, many old people suffer from deterioration of the head of the femur which must then be replaced by means such as a ball-and-socket prosthesis. The prosthesis comprises a male portion generally constituted by a portion of a sphere, and a female portion in the form of a cup, complementary to the portion of the sphere and having the same radius, the male portion being retained in the female portion by any appropriate means, in particular by the muscles and tendons of the patient in whom the prosthesis is implanted.

Amongst prostheses of this type, those intended more particularly for replacing hip joints comprise, in outline, two portions: a spherical or similar head mounted by any appropriate means on a fixing peg for implanting in a long bone such as the femur; and a cup which is complementary in shape to the head and suitable for being implanted in the pelvic bone.

Generally, implementation of the fixing peg presents no problem, neither with respect to its surface state nor with respect to the choice of material from which it is made. Likewise, the means currently used for the rotary co-operation between the ball and the cup give results which are quite satisfactory.

However, implementing the ball, in particular the portion of the sphere, provides much greater difficulties. Balls were initially made of metal. However, in view of some of the problems encountered, the person skilled in the art tried using ceramics, i.e. materials obtained by mixing powders of solid materials in organic additives such as suitable resins, and then raising the mixture to a high temperature.

At present, this is the form of implementation that is most commonly used, even though the joints obtained in this way do not have fully satisfactory constant strength. It has often been observed that when such a ball is subjected to a relatively severe shock, such as may occur when the patient in which it is implanted falls down, then the ball shatters.

In order to mitigate this drawback, special connection devices have been provided for associating such ball heads with the fixing pegs, however it is recognized that they still do not provide the desired degree of reliability.

The object of the present invention is to provide a ball-and-socket joint for a prosthesis combining the strength of metal with the friction qualities of materials such as ceramics, and which in addition does not present major difficulties of implementation.

More precisely, the present invention provides a ball-and-socket joint for a prosthesis, the joint comprising a male portion and a female portion, the male portion comprising a spherical ball and means for fixing said ball on a connection peg, the female portion comprising a cup having a concave spherical shape complementary to the ball, the joint being characterized by the fact that said ball is made of a material having a crystal structure.

Other characteristics and advantages of the present invention appear from the following description given with reference to the accompanying drawings given by way of non-limiting example, and in which.

Figure 1:
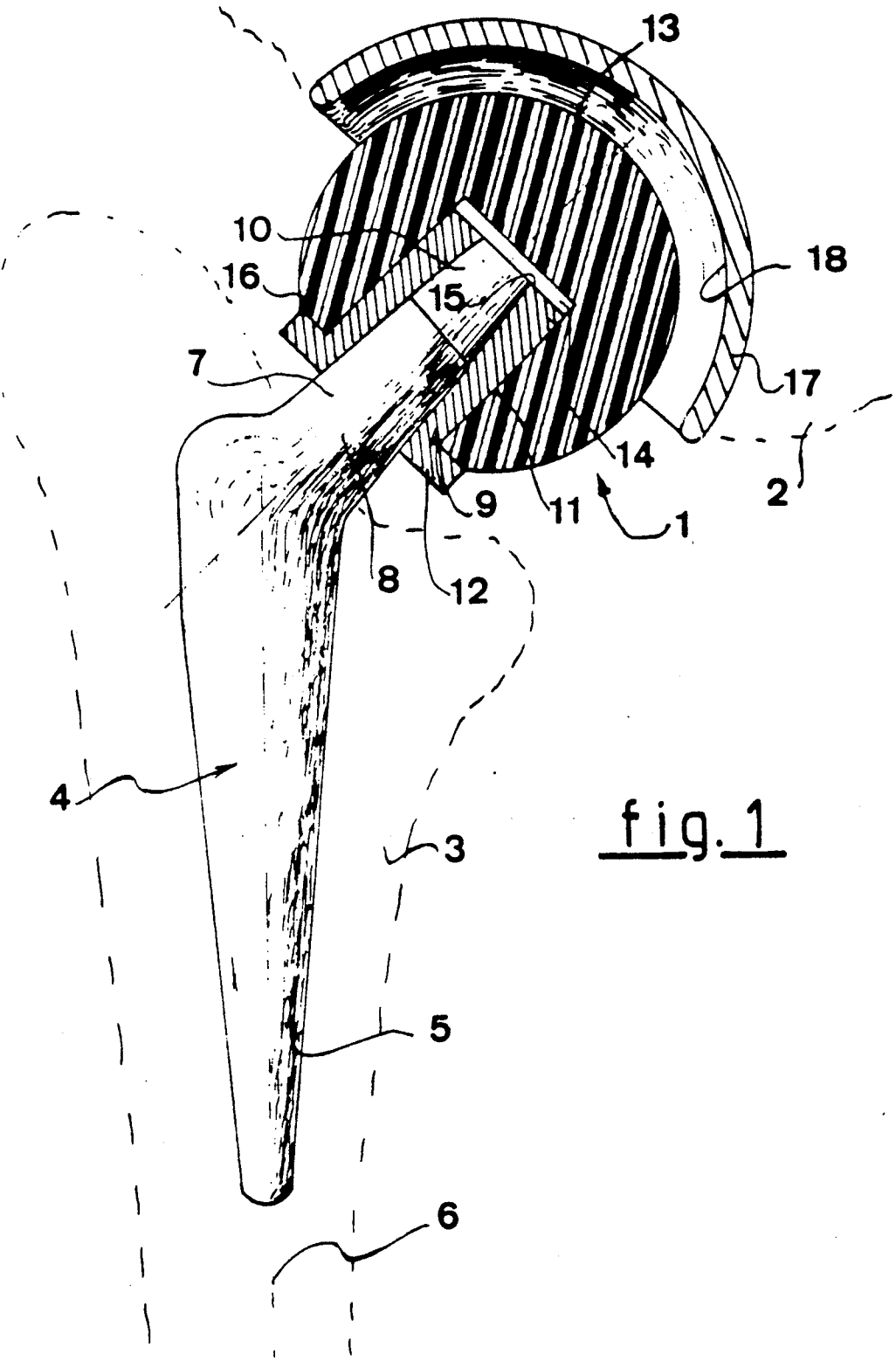
FIG. 1 is a section view through a first embodiment of a ball-and-socket joint of the invention for a hip prosthesis.

By way of example, FIG. 1 shows a ball-and-socket joint 1 for a hip prosthesis.

This hip prosthesis comprises, in particular, a fixing peg 4 suitable for being fixed in an orifice 5 made on the axis 6 of the femur 3.

Means for fixing the peg 4 in the femur 3 are known per se and are not described in greater detail herein.

At its projecting end 7, the fixing peg 4 generally includes a conical portion 8 suitable for being received in a connection bush 9 including a through opening 10 which is conical in shape, being complementary to the conical portion 8 of the peg 4.

The outside wall 11 of the connection bush 9 is advantageously cylindrical in shape and is delimited at a certain distance from the smallest cross-section of the conical portion 8, for example, by an outwardly directed flange 12.

A portion of a sphere or ball 13 constituting the male portion or "ball" of the ball-and-socket joint 1 is then fitted on the bush. This ball 13 includes a hollow housing 14 whose inside section is not less than the outside section of the wall 11 of the connection bush, and whose depth is not less than the distance between the flange 12 and the top end 15 of the bush 9.

In this way, the ball 13 is fitted over the bush 9 until the edge 16 of the ball 13 comes into contact with the flange 12. The ball is then fixed to the bush by any appropriate means, e.g. glue, brazing, etc., depending on the nature of the materials from which these two parts are made.

The joint 1 also includes a female portion or "socket" constituted by a cup 17 which constitutes a concave surface 18 of a spherical cap which is complementary in shape to the ball 13, thereby enabling the ball to engage the concave surface 18 with an ideal male-female fit.

The general ball-and-socket technique described above for implementing a hip prosthesis, for example, and as shown in FIG. 1, is well known per se. However, in order to improve the quality of the friction between the two portions of the joint and to increase the lifetime of such a joint, and therefore of the prosthesis including the joint, i.e. the length of time for which it can remain implanted, according to the main characteristic of the invention, the ball 13 is made of a material having a crystal structure, e.g. an alumina monocrystal including various quantities of doping materials such a iron, chromium, etc. For high quality applications, a diamond crystal could even be used. The socket portion of the joint constituted by the cup 17 may be made of a plastic material suitable for being implanted in the human body, e.g. one of the materials well known and commonly used in this application.

Monocrystals suitable for use in making balls 13 are relatively easily obtained, in particular when using a material based on alumina, by growing the monocrystal from a monocrystal seed, e.g. using the Czochralski method.

Experiments performed on such balls have shown that this type of implementation is fully satisfactory, both as to finish and as to strength, and they have shown that prostheses made in this way are much more reliable than prior art prostheses.

The monocrystals used are of the sapphire, ruby, etc., type and it must be admitted that such materials are relatively difficult to machine, in particular for making the hollow housing 14 in the ball 13 as shown in FIG. 1. Such "internal" machining requires special, very high quality tooling to be used and makes it difficult to inspect the state of the surface inside the housing since this surface is difficult of access for apparatuses capable of performing such inspection.

Figure 2:
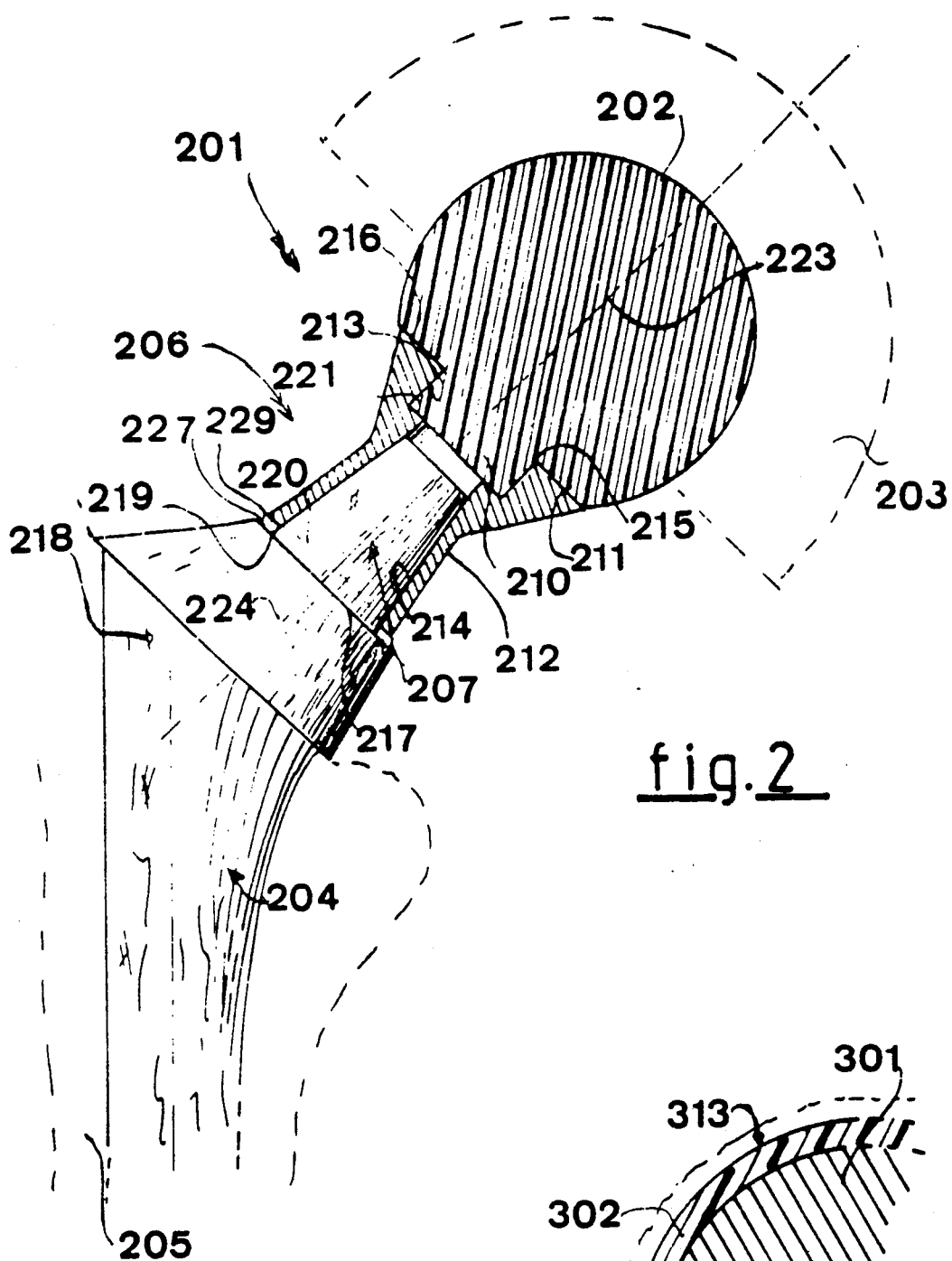
FIG. 2 is a section view through a second embodiment of a ball-and-socket joint of the invention, likewise for a hip prosthesis.

The embodiment shown in FIG. 2 mitigates these drawbacks by presenting a ball structure which is easier to implement than the prior art prosthesis structure, and is particularly advantageous when using a ball made of crystal material while also making it easier to inspect the state of the machined surfaces, in particular to ensure maximum fixing reliability to the prosthesis so as to avoid too-frequent surgical operations.

FIG. 2 shows an embodiment of a spherical head or ball 202 which is specially designed for a hip prosthesis 201 and which has the above-mentioned advantages. The ball 202 is suitable for rotating in a cup or cotula 203. The prosthesis 201 also includes a fixing peg 204 suitable for being implanted in the medullar canal of a long bone 205 such as a femur, together with connection means 206 for connecting the ball 202 to one of the ends 207 of the peg 204.

The connection means 206 comprise a cylindrical projection portion 210 projecting axially from a flat 211 formed in the ball 202, and a bush 212 having two bores 213 and 214. A first bore 213 is complementary in section to the projecting portion 210 which is fitted into said first bore 213, and the second bore 214 is substantially complementary in section to the end 207 of the fixing peg 204 which is, likewise, fitted in said second bore.

In an advantageous embodiment, the projecting portion 210 is smaller in section than the diameter of the flat 211 so as to define a bearing surface on the flat against which a portion of the bush 212 can be brought to bear as described below. Still for the purpose of obtaining a structure which is easy to obtain by machining, the projecting portion 210 and the first bore 213 are advantageously circular symmetrical in shape.

In order to allow the bore to absorb as large a quantity as possible of the forces to which a prosthesis implanted in a human body is generally subject, prior to transmitting them to the cotula, the outside opening 215 of the first bore 213 is delimited by an outside shoulder 216 in the form of a circular ring whose outside diameter is equal to or slightly less than the outside diameter of the flat 211. In this way, the spherical head bears firmly against the sleeve 212 via a first relatively large area.

In the advantageous embodiment shown, the end 207 of the fixing peg 204 is machined to have the shape of a truncated circular cone whose larger base 217 defines the connection area between the body 218 of the peg and the end 207 itself.

In this case, the second bore 214 is likewise substantially in the form of a frustoconical circular cone but its angle at the apex is slightly less than that of the portion of a cone defining the end 207, while having a larger base 219 whose cross-section is equal to one of the cross-sections at said end of the fixing peg, e.g. a section in the vicinity of that which is indicated by dashed lines 220 in FIG. 2.

It is mentioned above that the spherical head bears against a first shoulder 216 on the bush. In order to distribute the forces exerted on the prosthesis better still, the bearing surface of the prosthesis head is increased by forming an inwardly directed shoulder 212 at the bottom of the first bore 213 and situated at a distance from the outside opening 215 of the first bore which is equal to the height of the projecting portion 210.

In order to make mechanical implementation of such a bush as easy as possible, it is advantageous for the inside ends of the first and second bores 213 and 214 to coincide, as shown in FIG. 2, and also to ensure that the axes of symmetry 223 and 224 of these two bores coincide. Further, the frustoconical lateral surface of the second bore is made in such a manner that the diameter of its small base is smaller than the diameter of the first bore. This difference in cross-section thus ensures that the above-defined inwardly-directed shoulder 221 is formed directly during machining.

As mentioned above, the projecting portion 210 is fixed to the ball 202. However, one of the advantageous ways of obtaining this result is to form the ball and the projecting portion integrally in the same block of material, e.g. a monocrystal such as ruby, sapphire, etc.

The ball of the ball-and-socket prosthesis described above and shown in FIG. 2 is assembled as follows.

Once all three parts: ball, bush, and fixing peg, have been made, then the ball 202 and its projecting portion 210 is engaged with the bush 212 so that the projecting portion penetrates into the first bore 213 of the bush and is fixed thereto by any appropriate means, in particular gluing, welding, or brazing, depending on the natures of the materials constituting each of these two parts.

The end 207 of the fixing peg 204 is then engaged in the second bore 214 of the bush until the edge of the large base 210 of this second bore makes contact with the surface of the truncated cone defining the end of the peg. By applying additional force to engage the part, the wall of the bush is deformed around the second bore until the conical shape of said bore becomes substantially equal to that of the end of the fixing peg, with the inside wall of the bore then being an ideal fit around the surface of the end 207 of the fixing peg. This makes it possible to fix the bush and the bore securely on the fixing peg, by virtue of a clamping effect which is essentially due to the elasticity of the material used for making the bush, in particular.

The structure of the ball of the prosthesis as described above presents many advantages. Firstly it is easier to machine a block of very hard material using tools such as diamond grindstones for the purpose of obtaining projecting portions even if small, than it is to machine such a block with drills for obtaining housings therein. Further, since all of the machined surfaces of the balls and the projecting portions are external, it is much easier to inspect them for defects and qualities than it is to inspect inside surfaces.

Finally, this structure does not require any drilling into the bulk of the bore, and thus contributes to limiting the presence of points of weakness in this prosthesis head, thereby obtaining a corresponding increase in the reliability of this product.

Nevertheless, the structure for the head of a prosthesis as described above can be further improved. This improvement is constituted by a shoulder 227 situated level with the larger base 217 of the frustoconical end 207 of the peg 204. This shoulder can then constitute an abutment for limiting the extent to which the end 207 can be thrust into the second bore 214 of the bush 212. This limitation thus prevents excessive radial force being applied to the wall of the bore 214, thereby increasing the lifetime of the bush.

Naturally, in this case, the bush should be designed, in particular as a function of the material from which it is made, so as to ensure that the thickness of the wall of the second bore 214 imparts sufficient elasticity in deformation to ensure firstly that the circular ring 229 surrounding the larger base 219 of said second bore comes into abutment against the shoulder 227, and secondly that said wall is capable of exerting sufficient clamping force on the frustoconical end of the peg to ensure that the bush is securely fixed thereon.

In both of the embodiments described and shown above, the ball is made of a block of crystal material, or of monocrystalline material. However, it is obvious that in order to obtain such a portion of a sphere it is necessary to begin with a monocrystal which is large enough to be worked and machined down to the desired final shape. Although, in some cases such as for a knee prosthesis a spherical shape is required only over a small portion of the prosthesis, in general the radius of the sphere is relatively large and the quantity of starting material is always considerable. In order to mitigate this drawback which essentially gives rise to high cost, another object of the present invention is to provide a ball-and-socket joint structure enabling the cost of the prosthesis to be reduced.

Figure 3:
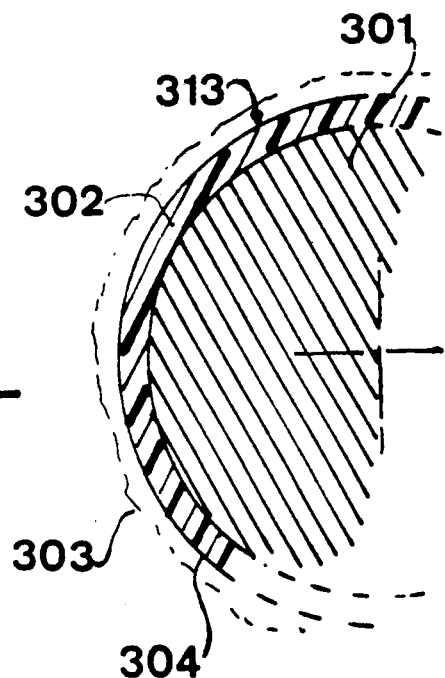
FIG. 3 is a diagrammatic section through an advantageous structure for a ball-and-socket joint of the invention.

In this case, as shown in FIG. 3, the spherical head 313 is essentially made up of two portions 301 and 302. The portion 301 constitutes a central core of rigid material, e.g. a metal such as steel, an alloy based on titanium, etc., which is already machined to be substantially spherical in shape, but which is smaller in diameter than the diameter required for the final ball of the joint.

A monocyrstaline layer 302 is then deposited on this central core, e.g. by the physical vapor deposition technique (known under the abbreviation PVD). This type of deposit is obtained, either by evaporation on its own, with the vapor condensing on the support, i.e. the spherical surface of the central core 301, or else by cathode sputtering, i.e. bombarding crystal material with gas ions conveying an electric discharge, and the vapor subsequently condensing on the core 301.

At least one other method may be useful in depositing the monocrystalline layer 302 on the central core 301, namely the chemical vapor deposition technique known in the art by the abbreviation CVD. In outline, this method consists in obtaining a deposit by means of a chemical reaction between a volatile compound to be deposited and the substrate or support.

In the present case, the method used is that which is best adapted to the crystal material in question and to the material constituting the central core 301.

The deposit is made up to a thickness 303 which is greater than the thickness 304 required for obtaining the final diameter of the ball, and the layer 302 is then machined in order to obtain the desired shape and size.

This embodiment is advantageous since it requires a small quantity only of crystal material, thereby reducing the cost price of such a prosthesis.

I claim:

1. An implantable joint prosthesis comprising:
   a ball member configured for rotation in a cotula, said ball member having one end forming a substantially planar surface with a projection portion extending axially outwardly therefrom;
   a shank member adapted to be implanted in a bone, said shank member having one end configured to be coupled to said ball member;
   a connection member for coupling said shank member to said ball member, said connection member comprising a bush having first and second bores formed therein, said first bore having a cross-section complementary to a cross-section of said projection portion and said second bore having a cross-section complementary to a cross-section of said one end wherein the projection portion engages aid first bore and the one end engages the second bore thereby coupling said shank member to said ball member.

2. A joint according to claim 1, wherein said projecting portion (210) is smaller in section than the diameter of the flat (211).

3. A joint according to claim 1, wherein that said projecting portion (210) and said first bore (213) are advantageously in the form of circular cylinders.

4. A joint according to claim 2, wherein the opening (215) of said first bore defines an outside shoulder (216) in the form of a circular ring having an outside diameter which is equal to or slightly less than the diameter of the flat (211).

5. A joint according to claim 1 wherein said one end (207) of said fixing peg (204) is in the form of a truncated circular cone having a larger base (217) defining the connection area between the body (218) and said one end (207) of said fixing peg.

6. A joint according to claim 5, wherein said second bore (214) is substantially in the form of a truncated circular cone having an apex and an angle at the apex which is slightly less than an apex angle of said truncated cone defining said one end (207) of said connection peg, and said second bore (214) having a larger base (219) equal in area to a section (220) of said truncated cone.

7. A joint according to claim 6, wherein said end (207) of said connection peg includes a shoulder (227) situated level with said larger base (217) of said core, said shoulder (227) constituting an abutment for limiting the extent to which said end (207) is engaged in said second bore (214) of the bush (212).

8. A joint according to claim 1, wherein said first bore has a radially inwardly directed shoulder (221) at an end situated at a distance from the opening (215) of said first bore which is equal to the axial length of said projecting portion.

9. A joint according to claim 1 wherein the ends of said first and second bores (213, 214) conincide.

10. A joint according to claim 3, wherein the axes of revolution (223, 224) of said two bores coincide, the diameter of a small base of the frustoconical shaped second bore being smaller than the diameter of the first bore.

11. A joint according to claim 1, wherein said ball (202) and said projecting portion (210) are integrally formed of the same block of material.

12. A joint according to claim 1, wherein said ball (313) comprises at least two portions: a first portion (301) constituting a central core; and a second portion (302) constituting a layer deposited on the first portion.

13. A joint according to claim 12, characterized by the fact that said layer is made of a material having a crystalline structure.

* * * * *